(12) United States Patent
Malher

(10) Patent No.: US 9,393,138 B2
(45) Date of Patent: Jul. 19, 2016

(54) DEVICE FOR PLACEMENT OF A SELF-EXPANDING ENDOPROSTHESIS

(75) Inventor: Etienne Malher, Nancy (FR)

(73) Assignee: MS TECHNIQUES, Pompey (FR)

(*) Notice: Subject to any disclaimer, the term of this patent is extended or adjusted under 35 U.S.C. 154(b) by 517 days.

(21) Appl. No.: 10/859,601

(22) Filed: Jun. 3, 2004

(65) Prior Publication Data
US 2005/0273148 A1 Dec. 8, 2005

(51) Int. Cl.
*A61F 2/06* (2013.01)
*A61F 2/958* (2013.01)

(52) U.S. Cl.
CPC ......... *A61F 2/958* (2013.01); *A61F 2002/9583* (2013.01)

(58) Field of Classification Search
CPC .............. A61F 2/95; A61F 2002/9665; A61F 2002/9505–2202/9534; A61F 2/954; A61F 2/958; A61F 2002/9583–2002/9586; A61F 2/962–2/966; A61F 2/97
USPC .................................. 623/1.11, 1.12; 606/108
See application file for complete search history.

(56) References Cited

U.S. PATENT DOCUMENTS

| | | | | |
|---|---|---|---|---|
| 5,171,299 A | * | 12/1992 | Heitzmann et al. | 604/100.03 |
| 5,201,757 A | * | 4/1993 | Heyn et al. | 606/198 |
| 5,743,874 A | * | 4/1998 | Fischell et al. | 604/103.1 |
| 5,846,246 A | * | 12/1998 | Dirks et al. | 606/108 |
| 6,030,413 A | | 2/2000 | Lazarus | |
| 6,059,809 A | * | 5/2000 | Amor et al. | 606/194 |
| 6,156,005 A | * | 12/2000 | Theron | 604/96.01 |
| 6,241,758 B1 | * | 6/2001 | Cox | 623/1.11 |
| 6,364,900 B1 | * | 4/2002 | Heuser | 623/1.11 |
| 6,395,014 B1 | * | 5/2002 | Macoviak et al. | 606/200 |
| 6,613,075 B1 | * | 9/2003 | Healy | A61F 2/95 606/108 |
| 6,712,832 B2 | * | 3/2004 | Shah | 606/192 |
| 7,309,350 B2 | * | 12/2007 | Landreville et al. | 623/1.11 |
| 2001/0051784 A1 | * | 12/2001 | Brisken et al. | 604/22 |
| 2002/0103525 A1 | * | 8/2002 | Cummings | 623/1.11 |
| 2002/0173817 A1 | * | 11/2002 | Kletschka et al. | 606/194 |
| 2002/0183826 A1 | * | 12/2002 | Dorn et al. | 623/1.11 |
| 2004/0024448 A1 | * | 2/2004 | Chang et al. | 623/1.42 |
| 2004/0127912 A1 | * | 7/2004 | Rabkin | A61F 2/95 606/108 |
| 2004/0215229 A1 | * | 10/2004 | Coyle | 606/200 |

FOREIGN PATENT DOCUMENTS

| | | |
|---|---|---|
| EP | 699 451 A2 | 3/1996 |
| WO | WO 99 47075 A1 | 9/1999 |

* cited by examiner

*Primary Examiner* — Katherine Rodjom
*Assistant Examiner* — Lindsey Bachman
(74) *Attorney, Agent, or Firm* — Sughrue Mion, PLLC

(57) ABSTRACT

Device for placement of a self-expanding endoprosthesis, extending between a proximal end and a distal end. An outer sheath (1) is able to keep an endoprosthesis (21) in radial contraction. A mandrel (4), which extends axially inside the outer sheath, is movable axially with respect to the outer sheath and has, at its distal end (3), a chamber (2) able to receive an endoprosthesis (21) in radial contraction, the chamber being delimited at its distal end by an atraumatic tip (6) which can occlude the outer sheath. The atraumatic tip (6) is made of elastomer material that forms a thin-walled inflatable chamber (10) which can be inflated by a pressure insufficient to widen a channel intended to receive the prosthesis, and into which there leads a lumen (9) extending from the distal end to the proximal end of the mandrel for passage of an inflation fluid.

10 Claims, 3 Drawing Sheets

DEVICE FOR PLACEMENT OF A SELF-EXPANDING ENDOPROSTHESIS

BACKGROUND OF THE INVENTION

The present invention relates to a device for placement of a self-expanding endoprosthesis.

Endoprostheses are medical implants of generally tubular shape, made of metal or of polymer material and intended to keep open a channel which has a tendency to close under the effect of a disease (tumor, atheromatous plaque, etc.). This channel can, for example, be an artery, a vein, an airway, a urinary passage or a bile duct.

These implants are introduced in a contracted state so that they can be brought to the implantation site with the least possible trauma. They are then dilated to their final size either by plastic deformation or by their inherent resilience. Implants dilated to their final size by virtue of their inherent resilience constitute endoprostheses referred to as self-expanding, described for example by Hans Ivar Wallsten in patent FR 2 525 896.

These endoprostheses are put in place with the aid of a device consisting principally of:
- an outer sheath which allows the endoprosthesis to be maintained in its compressed configuration. This sheath extends from its proximal end, which remains outside the body, to its distal end where the endoprosthesis is situated.
- an inner mandrel which is of a length adapted to that of the sheath and slides inside the latter and, by means of a relative translation movement, allows the endoprosthesis to be pushed out of the sheath. This mandrel is joined temporarily to the endoprosthesis either by a fine layer of flexible material which adheres to the mandrel and in which the endoprosthesis will be embedded, the configuration described by John H. Burton et al. in the patent EP 0 408 245, or by an abutment which comes into contact with the endoprosthesis, as described by David J. Wilson et al. in the patent EP 1 025 813, or by other mechanical devices such as, for example, the one described by Brett W. Cryer in the patent WO 02/41805. This mandrel passes through the endoprosthesis and terminates in a flexible and rounded end which fits the end of the sheath and permits advance of the assembly during introduction without risk of damaging the tissues.

In order to facilitate the travel of the instrument as it is advanced toward the zone to be treated, a guide wire is first introduced as far as this zone.

Two configurations are known:
- the configuration referred to as coaxial, in which the mandrel is pierced from end to end to permit passage of the guide wire along its entire length.
- the configuration referred to as "rapid exchange" described by Stephen R. Healy et al. in the patent EP 1 095 634. In this configuration, the mandrel has a passage between the distal end and a lateral opening situated a certain distance from this end. Instead of running through the whole device, the guide wire extends only along this short distance.

To put the prosthesis in place, the practitioner first introduces the guide wire into the channel through and beyond the zone to be treated, then he introduces that end of the guide wire remaining outside the body into the distal part of the mandrel. He then slides it until it emerges either through the proximal end—coaxial configuration—or through the lateral opening—"rapid exchange"—then moves the device along this guide until the distal end is level with the zone to be treated, so as to position the endoprosthesis in line with the zone to be treated.

He then executes a relative translation movement between mandrel and sheath, which allows the endoprosthesis to emerge from the sheath. During this translation movement, he endeavors to keep the mandrel fixed relative to the channel while pulling back the sheath so that the endoprosthesis remains in line with the zone to be treated. When the endoprosthesis is entirely deployed, he can withdraw the device.

Correct positioning of the endoprosthesis is an indispensable factor in the success of the operation. To achieve this, it is absolutely essential to control the stability of the mandrel in its distal part throughout the deployment procedure.

To achieve this result, maneuvering grips have been proposed which permit a return movement of the sheath while maintaining the mandrel fixed in relation to the operating surgeon's hand. A device of this kind is described by Roy Sullivan in the U.S. Pat. No. 5,968,052.

The main failing of this type of instrument is that it cannot guarantee correct control of the movement of the distal part, particularly in cases where the instrument follows several curves inside the channels which lead it to the zone to be treated. The desired behavior of the instrument is such that the mandrel remains fixed in its distal part as in its proximal part and the sheath retreats in its distal part as in its proximal part. However, a different behavior may be caused by, for example, considerable friction between the outer face of the sheath and the wall of the channel to be treated. In this case, the movement of the sheath is correct at the proximal area, but it remains immobile in relation to the zone to be treated at its distal end, with the result that the compensation of the movement is effected by a modification of the curves of the instrument and it is the mandrel which, on leaving the sheath, is displaced relative to the channel to be treated.

This phenomenon is made still worse in cases where a moving organ is being treated, for example the coronary arteries.

It will be noted that placement of the endoprosthesis is often preceded by angioplasty intended to dilate the channel to be treated. This angioplasty is performed with the aid of a catheter comprising an angioplasty balloon made of a resistant and fairly inelastic material, so that it can be inflated to a defined diameter by means of a high pressure which can exceed 10 bar.

So as not to have to use two successive catheters, it has been proposed, especially in the patent application EP 0 699 451, to use an integrated catheter having, at its distal end, an angioplasty balloon and a means of deploying a self-expanding endoprosthesis. However, such a catheter does not solve the problem of positioning at the moment of placement of the endoprosthesis.

During deployment, the dilation balloon is situated downstream of the treated zone, that is to say in a healthy and much narrower channel. Because of the construction of the balloon, inflation, even at a very low pressure, causes dilation of the channel, which is a very unfavorable factor in terms of the phenomenon of restenosis. The patent application mentioned above indicates that the balloon remains deflated during deployment.

A catheter comprising a balloon of the angioplasty balloon type has also been proposed, in particular in the U.S. Pat. No. 6,030,413, for placing grafts held by staples. However, such a catheter is not suitable for placement of self-expanding endoprostheses.

SUMMARY OF THE INVENTION

The object of the invention is to make available a device for deploying a self-expanding endoprosthesis whose mandrel can be immobilized in its distal part at the place in the channel where the practitioner has chosen to perform the deployment procedure, this element being able to be activated and deactivated as and when desired by the practitioner.

To this end, the invention proposes a device for placement of a self-expanding endoprosthesis, the device extending between a proximal end and a distal end and comprising:
  an outer sheath able to keep an endoprosthesis in radial contraction,
  a mandrel which extends axially inside the outer sheath, is movable axially with respect to the outer sheath and has, at its distal end, a chamber able to receive an endoprosthesis in radial contraction, said chamber being delimited at its distal end by an atraumatic tip which can occlude said outer sheath, wherein the atraumatic tip is made of elastomer material and comprises a thin-walled inflatable chamber which can be inflated by a pressure insufficient to widen a channel intended to receive the prosthesis, and into which there leads a lumen extending from the distal end to the proximal end of the mandrel for passage of an inflation fluid.

The inflatable chamber of the atraumatic tip can preferably be inflated by a pressure of less than 1 bar.

The elastomer material from which the atraumatic tip is made is for example an elastomer chosen from silicone, natural rubber, polyurethane and polyether block amide.

The mandrel can comprise a second lumen extending from the distal end to the proximal end for passage of a guide wire, said second lumen continuing in the axis of the atraumatic tip.

The lumen of the mandrel for circulation of an inflation fluid can have a diameter sufficient to permit passage of a guide wire and circulation of an inflation fluid simultaneously. The atraumatic tip can then comprise an axial hole for the guide wire, the inner wall of which axial hole comprises at least one bead in order to ensure leaktightness of the contact with the guide wire.

The device can comprise a coaxial sheath, situated inside the lumen of the mandrel permitting circulation of an inflation fluid without occluding said lumen, extending from the distal end of the mandrel and leading outside the device via an opening situated between the distal end and the proximal end, and permitting passage of a guide wire, said sheath continuing in the axis of the atraumatic tip so as to ensure leaktightness with the mandrel and leave free the passage of the guide wire.

The invention also relates to a method for placing a self-expanding endoprosthesis in a channel with the aid of a device according to the invention.

According to this method:
  the device is introduced into the channel as far as the zone to be treated;
  a defined volume of inflation liquid is introduced into the chamber of the atraumatic tip in such a way as to form a balloon which immobilizes the tip of the device relative to the channel;
  the endoprosthesis is freed by pulling back the outer sheath;
  the balloon is deflated and the device is withdrawn.

BRIEF DESCRIPTION OF THE INVENTION

The invention will now be described in greater detail but in a limiting manner with reference to the attached figures, where:

DETAILED DESCRIPTION OF THE INVENTION

Figure 1A:
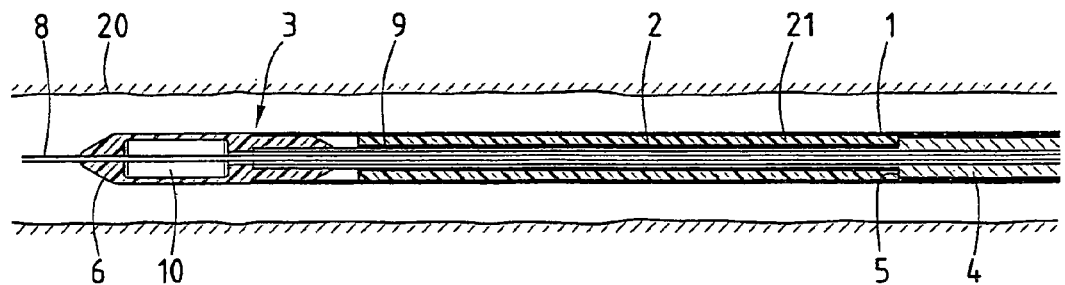
FIGS. 1A, 1B, 1C, 1D and 1E show, in longitudinal section, the distal end of a device for deploying a self-expanding endoprosthesis inside a channel intended to receive the endoprosthesis, at the five main stages of the deployment of the endoprosthesis.
Figure 1B:
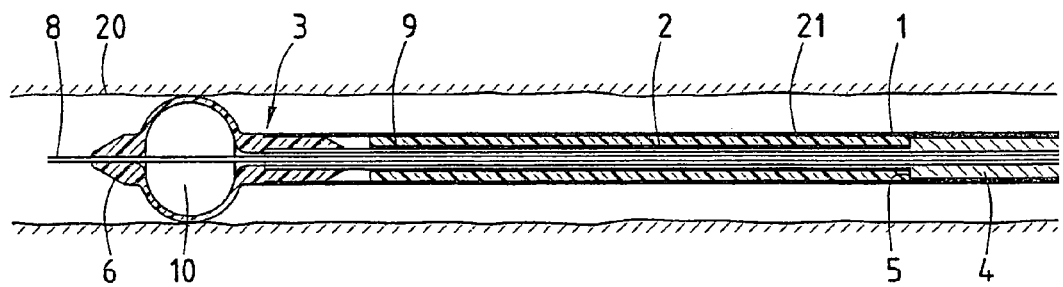
Figure 1C:
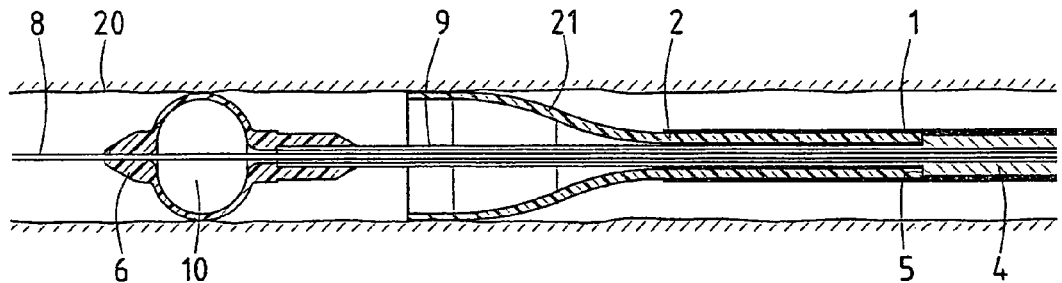
Figure 1D:
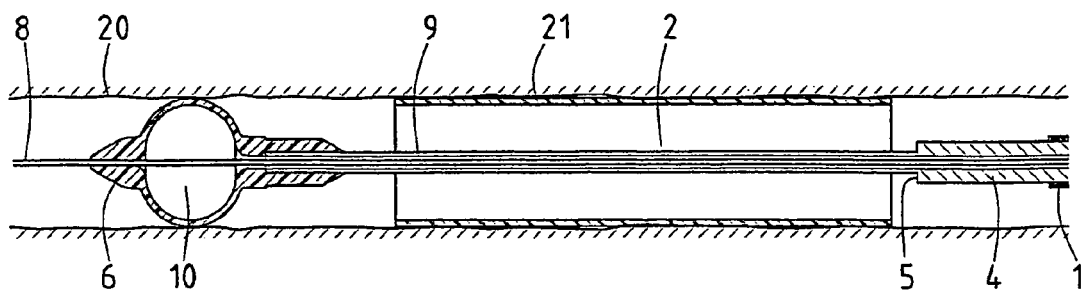
Figure 1E:
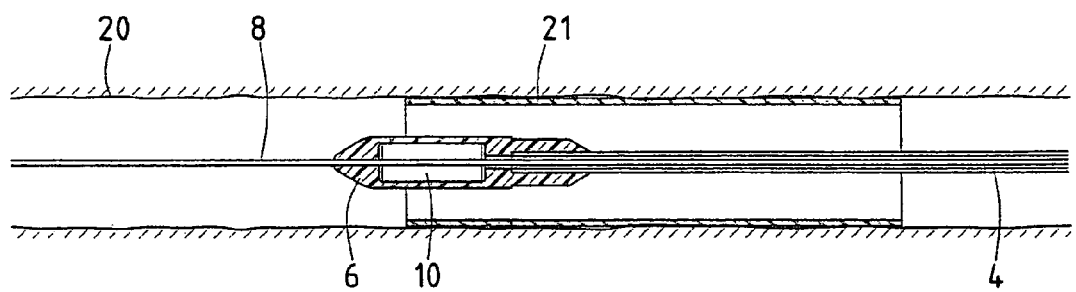

The device for placement of a self-expanding endoprosthesis consists of:
  an outer sheath 1 which allows an endoprosthesis 21 to be maintained in its compressed configuration. This sheath extends from its proximal end, which remains outside the body, to its distal end 3, where the endoprosthesis 21 is situated.
  an internal mandrel 4 with a length adapted to that of the sheath 1 and extending axially inside the sheath, sliding in the latter and, by means of a relative translation movement, allowing the endoprosthesis 21 to be pushed out of the sheath. This mandrel is joined temporarily to the endoprosthesis by an abutment 5 which comes into contact with the endoprosthesis, such as is described by David J. Wilson et al. in the patent EP 1 025 813.

This mandrel passes through the endoprosthesis and ends in an atraumatic tip 6 which fits the end of the sheath 1, delimiting with the abutment 5 a chamber 2 which can receive an endoprosthesis 21. This atraumatic tip permits advance of the assembly during introduction without risk of damaging the tissues.

In order to facilitate the travel of the device for placement of an endoprosthesis as it is advanced toward the zone to be treated, a guide wire 8 is first introduced as far as this zone, and at least the distal end of the device for placement of an endoprosthesis can slide along this wire.

In a first embodiment of the guide wire, the mandrel comprises a lumen 9 or 9'A extending along its entire length in order to permit passage of the guide wire along the entire length of the mandrel.

In a second embodiment of the guide wire, referred to as "rapid exchange" described by Stephen R. Healy et al. in the patent EP 1 095 634, the mandrel comprises a lumen 9B extending from the distal end of the device for placement of an endoprosthesis as far as a lateral opening 14 provided in the wall of the device for placement of an endoprosthesis, and thus leading to the outside between the distal end and the proximal end of the device. In the embodiment, the guide wire extends along only a short length of the device for placement of a prosthesis, which makes maneuvering of the device easier.

The atraumatic tip 6 is made of a flexible and elastic material of the elastomer type, for example of the crosslinked elastomer type such as silicone or natural rubber, or of the thermoplastic elastomer type such as polyurethane or polyether block amide.

This atraumatic tip 6 comprises a thin-walled chamber 10 which can be inflated at moderate pressure to form a balloon. This balloon is comparable to the balloon of a Fogarty catheter, that is to say it is not intended, and is not able, to serve to dilate the channel in which it is placed. This balloon is intended to be inflated by a liquid such as physiological serum or contrast liquid, conveyed via a lumen extending the entire length of the mandrel 4, and delivered via a syringe of limited volume (not shown itself) so as to limit the expansion of the balloon.

With such a device, the pressure of inflation of the balloon is insufficient to dilate a channel comprising atheroma. The volume of liquid injected causes dilation of the balloon until contact with the walls of the channel, then the excess volume is absorbed by the elongation of the balloon. This pressure can be less than 1 bar.

Several embodiments of the atraumatic tip and of its connection to the mandrel are possible. Three embodiments are shown in FIGS. 2, 3 and 4.

Figure 2:
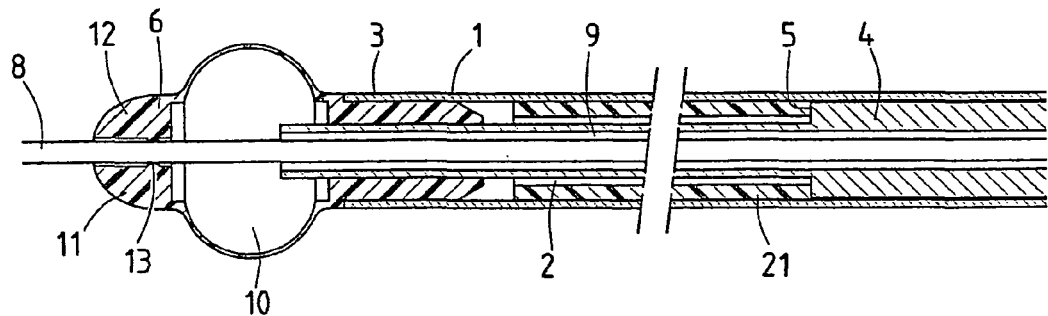
FIG. 2 is an enlarged cross section of the distal end of a first embodiment of a device for deploying an endoprosthesis.

In a first embodiment, shown in FIG. 2, the mandrel comprises a single lumen 9 of sufficient diameter for passage both of the guide wire 8 and of the inflation liquid. This lumen 9 leads into the chamber 10 intended to form a balloon. The guide wire 8 passes through the chamber 10, then the end 11 of the atraumatic tip via an axial hole 12 which comprises an internal bead 13 intended to ensure leaktightness of the contact with the guide wire.

Figure 3:
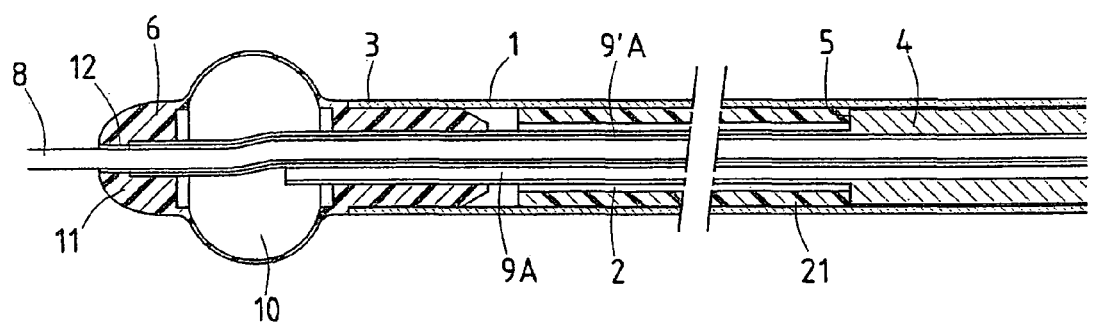
FIG. 3 is an enlarged cross section of the distal end of a second embodiment of a device for deploying an endoprosthesis.
Figure 4:
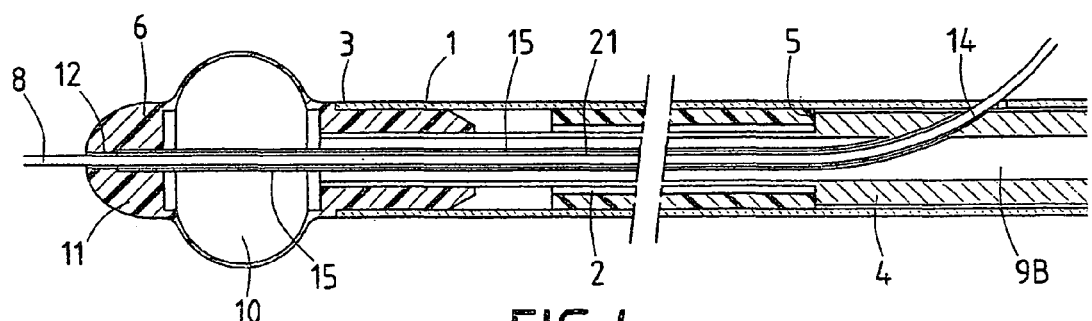
FIG. 4 is an enlarged cross section of the distal end of a third embodiment of a device for deploying a self-expanding endoprosthesis.

In a second embodiment shown in FIG. 3, the mandrel 4 is continued as far as the end 11 of the atraumatic tip 6.

It comprises a first axial lumen 9'A intended to receive the guide wire 8 leading into the axial hole 12 of the end 11 of the atraumatic tip 6, and a second lumen 9A parallel to the first and intended to receive the inflation liquid and leading into the chamber 10 intended to form a balloon.

In a third embodiment, shown in FIG. 4, corresponding to a device of the "rapid exchange" type, the mandrel 4 comprises a lumen 9B intended to receive the inflation liquid, and in its distal part to additionally receive the guide wire 8 which, at the proximal end, emerges from the mandrel via a lateral opening 14. The guide wire passes through the end 11 of the atraumatic tip 6 via an axial hole 12, and the leaktightness is ensured by a sheath 15 in which the guide wire 8 can slide. This sheath 15 extends from the end 11 of the atraumatic tip 6 as far as the lateral opening 14 provided in the mandrel to allow the guide wire to emerge from the side.

In the embodiments which have been described above, the endoprosthesis is maintained in place on the mandrel by way of an abutment 5. However, other embodiments forming part of the invention are possible. These are, for example, a mechanical device such as that described by Brett W. Cryer in patent application WO 02/41805, or a fine layer of flexible material which adheres to the mandrel and in which the endoprosthesis will be embedded, the configuration described by John H. Burton et al. in the patent EP 0 408 245.

In all cases, the outer sheath and the mandrel are connected, at their proximal ends, to grips known per se and permitting a movement of translation of the mandrel relative to the sheath.

The sequences of use of the device for placement of an endoprosthesis in a channel are represented in FIGS. 1A to 1E.

Step A: The device is advanced through the channel 20 to the zone to be treated.

Step B: The balloon 10 is inflated, which immobilizes the end of the mandrel 4.

Step C: The practitioner exerts a movement of withdrawal of the sheath 1 in its distal part by virtue of the immobilization of the distal part of the mandrel. The endoprosthesis 21 begins to deploy.

Step D: The sheath is fully withdrawn, the endoprosthesis 21 is released completely.

Step E: The balloon 10 is deflated, freeing the device, which is then withdrawn from the channel to be treated.

The invention claimed is:

1. A method for placing a self-expanding endoprosthesis (21) in a channel (20) with the aid of a device for placement of the self-expanding endoprosthesis, extending between a proximal end and a distal end, into the channel of a patient, the device comprising: an outer sheath (1) able to keep an endoprosthesis (21) in radial contraction, and a mandrel (4), which extends axially inside the outer sheath (1), is movable axially with respect to the outer sheath, has a chamber (2) which is configured to receive the endoprosthesis (21) in radial contraction, said mandrel being delimited at its distal end by an atraumatic tip (6), said atraumatic tip being configured to occlude said outer sheath, and having means for securing the position of an endoprosthesis relative to the mandrel, the atraumatic tip (6) comprising an axial hole (12) for passage of a guide wire, wherein the atraumatic tip (6) is made of an elastomer material and comprises a thin-walled inflatable chamber (10) which is configured to be inflated by a pressure of less than 1 bar to form an expanded shape, wherein a proximal end of the atraumatic tip is configured to be distal from a distal end of the endoprosthesis; and wherein a lumen (9, 9A, 9B) extends from a distal end to a proximal end of the mandrel (4) for passage of an inflation fluid and leads into the inflatable chamber (10), wherein the atraumatic tip (6) comprises a proximal portion and said inflatable chamber, said proximal portion fitting an end of said sheath, said atraumatic tip being movable axially relative to the sheath between a first position in which the proximal portion is located in the sheath, and a second position in which the proximal portion is located outside the sheath, the method comprising the steps of:
introducing the device into the channel (20) as far as the zone to be treated;
introducing a defined volume of inflation liquid into the inflatable chamber (10) of the atraumatic tip (6) in such a way as to form a balloon which immobilizes the tip of the device relative to the channel; wherein the inflation liquid is introduced into the inflatable chamber while the atraumatic tip is in the first position,
freeing the endoprosthesis by pulling back the outer sheath (1); and
deflating the balloon and withdrawing the device.

2. The method according to claim 1, wherein the sheath has a proximal end intended to remain outside the body of said patient.

3. The method according to claim 1, wherein said means for securing the position of the endoprosthesis relative to the mandrel is an abutment (5) of the mandrel, and
wherein a distance between the atraumatic tip (6) and the abutment of the mandrel remains constant between the first position and the second position such that a deployment position of the endoprosthesis is determined by a position of the atraumatic tip.

4. The method according to claim 1, wherein the elastomer material from which the atraumatic tip (6) is made is an elastomer chosen from silicone, natural rubber, polyurethane and polyether block amide.

5. The method according to claim 1, wherein the mandrel (4) comprises a second lumen (9A') extending from the distal end to the proximal end for passage of the guide wire (8), said second lumen continuing in the axis of the atraumatic tip.

6. The method according to claim 1, wherein the lumen (9) of the mandrel (4) for circulation of an inflation fluid has a diameter sufficient to permit passage of the guide wire (8) and circulation of an inflation fluid simultaneously.

7. The method according to claim 1, wherein the inner wall of the axial hole (12) of the atraumatic tip comprises at least one bead (13) in order to ensure leaktightness of the contact with the guide wire (8).

8. The method according to claim 1, further comprising the step of using a coaxial sheath (15), situated inside the lumen (9B) of the mandrel (4) permitting circulation of an inflation fluid without occluding said lumen, extending from the distal end of the mandrel and leading outside the device via an opening (14) situated between the distal end and the proximal end, said sheath (15) permitting passage of the guide wire (8), said sheath (15) continuing in the axial hole of the atraumatic tip (6) so as to ensure leaktightness with the mandrel and leave free the passage of the guide wire.

9. The method according to claim 1, wherein the device is configured to receive the endoprosthesis which is self-expanding.

10. The method according to claim 1, wherein the mandrel is movable axially with respect to the outer sheath for moving the endoprosthesis relative to the outer sheath by a relative translation movement of the mandrel.

\* \* \* \* \*